(12) United States Patent
Konetzki et al.

(10) Patent No.: US 7,250,426 B2
(45) Date of Patent: Jul. 31, 2007

(54) TIOTROPIUM-CONTAINING PHARMACEUTICAL COMBINATION FOR INHALATION

(75) Inventors: Ingo Konetzki, Warthausen (DE); Christopher J. Montague Meade, Bingen (DE); Michel Pairet, Biberach (DE); Michael P. Pieper, Biberach (DE)

(73) Assignee: Boehringer Ingelheim Pharma GmbH & Co KG, Ingelheim (DE)

( * ) Notice: Subject to any disclaimer, the term of this patent is extended or adjusted under 35 U.S.C. 154(b) by 61 days.

(21) Appl. No.: 10/717,868

(22) Filed: Nov. 19, 2003

(65) Prior Publication Data

US 2004/0132759 A1 Jul. 8, 2004

Related U.S. Application Data

(60) Provisional application No. 60/446,668, filed on Feb. 11, 2003.

(30) Foreign Application Priority Data

Nov. 29, 2002 (DE) .............................. 102 56 080

(51) Int. Cl.
| | |
|---|---|
| *A61K 31/47* | (2006.01) |
| *C07D 491/08* | (2006.01) |
| *C07D 451/02* | (2006.01) |

(52) U.S. Cl. ...................... 514/312; 546/157; 546/124; 546/89

(58) Field of Classification Search ................ 514/312; 546/157, 124, 89
See application file for complete search history.

(56) References Cited

U.S. PATENT DOCUMENTS

| 5,610,163 | A | 3/1997 | Banholzer et al. |
|---|---|---|---|
| 6,433,027 | B1 | 8/2002 | Bozung et al. |
| 6,455,524 | B1 | 9/2002 | Bozung et al. |
| 6,630,466 | B2 | 10/2003 | Bozung et al. |
| 6,777,423 | B2 | 8/2004 | Banholzer et al. |
| 6,890,517 | B2 | 5/2005 | Barth et al. |
| 6,908,928 | B2 | 6/2005 | Banholzer et al. |
| 2002/0137764 | A1 | 9/2002 | Barth et al. |
| 2002/0193392 | A1 | 12/2002 | Schmelzer et al. |
| 2002/0193394 | A1 | 12/2002 | Disse |
| 2003/0113269 | A1 | 6/2003 | Gavin et al. |
| 2003/0119802 | A1 | 6/2003 | Gavin et al. |
| 2003/0203918 | A1 | 10/2003 | Meade et al. |
| 2004/0002548 | A1 | 1/2004 | Bozung et al. |
| 2004/0039011 | A1 | 2/2004 | Disse |
| 2005/0147564 | A1 | 7/2005 | Barth et al. |
| 2005/0148562 | A1 | 7/2005 | Jung et al. |

FOREIGN PATENT DOCUMENTS

| EP | 04019003 | 8/2004 |
|---|---|---|
| EP | 05104702 | 5/2005 |
| EP | 05107266 | 8/2005 |
| EP | 05107267 | 8/2005 |
| WO | WO 00/75114 | * 12/2000 |
| WO | WO 01/78739 | 10/2001 |
| WO | WO 01/78741 | 10/2001 |
| WO | WO 02/38154 | 5/2002 |
| WO | WO 02/45703 | * 6/2002 |

* cited by examiner

*Primary Examiner*—D. Margaret Seaman
(74) *Attorney, Agent, or Firm*—Michael P. Morris; Mary-Ellen M. Devlin; Wendy Petka

(57) ABSTRACT

The present invention relates to new pharmaceutical compositions for inhalation containing one or more, preferably one, tiotropium salt combined with one or more pharmacologically acceptable acid addition salts of a compound of formula 2', wherein the groups $R^1$, $R^2$, $R^3$ and $R^4$ may have the meanings given in the claims and in the specification, processes for preparing them and their use in the treatment of respiratory complaints.

14 Claims, 3 Drawing Sheets

TIOTROPIUM-CONTAINING PHARMACEUTICAL COMBINATION FOR INHALATION

RELATED APPLICATIONS

Figure 1:
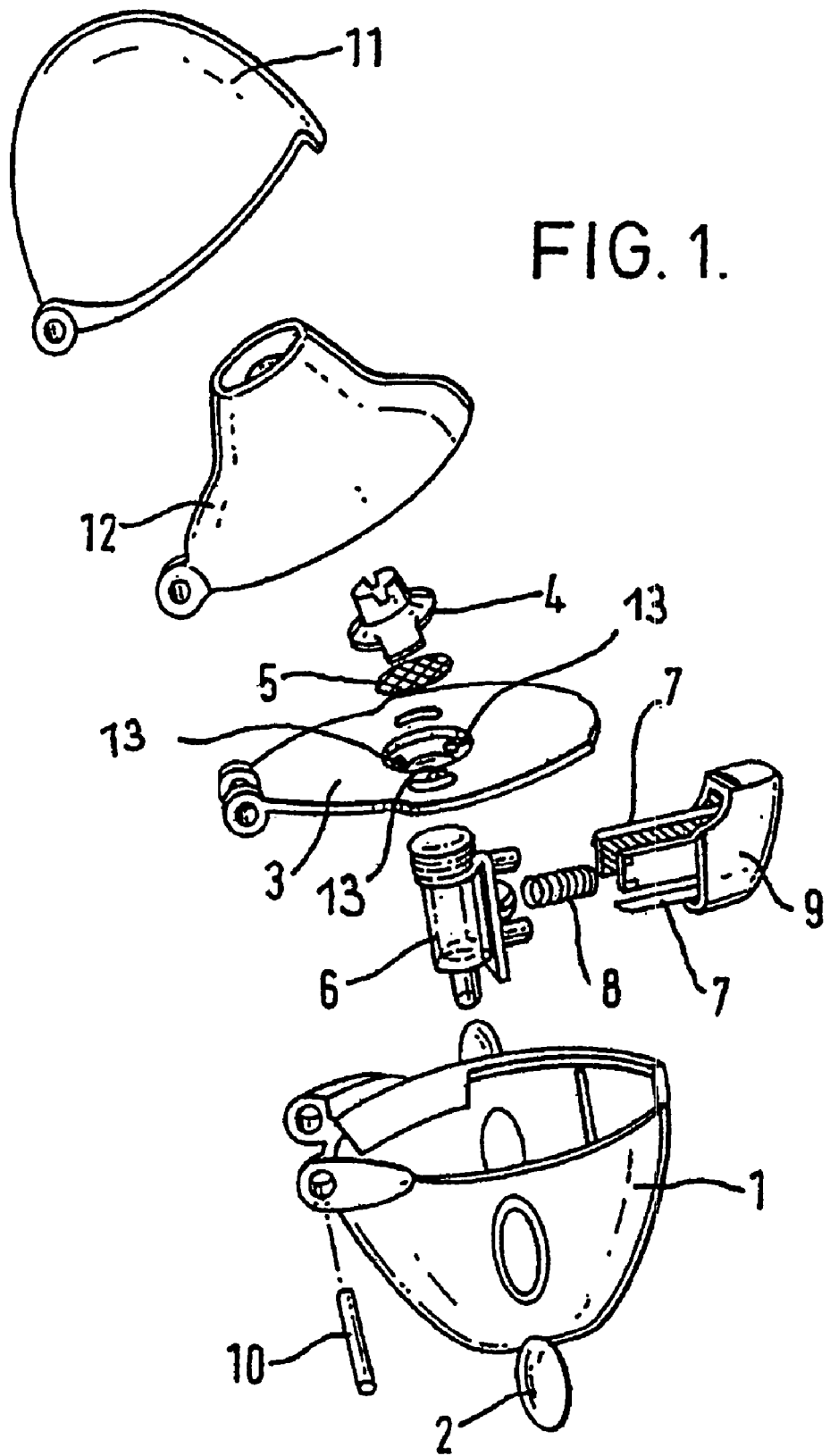

Benefit of U.S. Provisional Application Ser. No. 60/446,668, filed on Feb. 11, 2003 is hereby claimed.

FIELD OF THE INVENTION

The present invention relates to new pharmaceutical compositions for inhalation containing one or more, preferably one, tiotropium salt combined with one or more pharmacologically acceptable acid addition salts of a compound of formula 2', wherein the groups $R^1$, $R^2$, $R^3$ and $R^4$ may have the meanings given in the claims and in the specification, processes for preparing them and their use in the treatment of respiratory complaints.

BACKGROUND TO THE INVENTION

The compound tiotropium bromide, a salt of tiotropium, is known from European Patent Application EP 418 716 A1 and has the following chemical structure:

This compound may also be referred to by the chemical name (1α,2β,4β,5α,7β)-7-[(hydroxydi-2-thienylacetyl)oxy]-9,9-dimethyl-3-oxa-9-azoniatricyclo[3.3.1.0$^{2,4}$]nonane-bromide and has valuable pharmacological properties. The name tiotropium is to be interpreted within the scope of the present invention as a reference to the free cation 1'.

Tiotropium bromide, and other salts of tiotropium, are highly active anticholinergics and may therefore provide a therapeutic benefit in the treatment of asthma or COPD (chronic obstructive pulmonary disease).

Tiotropium salts are preferably administered by inhalation. Suitable inhalable powders packed into appropriate capsules (inhalettes) and administered by suitable powder inhalers may be used. Alternatively, it may be administered by the use of suitable inhalable aerosols. These also include powdered inhalable aerosols which contain, for example, HFA134a, HFA227 or mixtures thereof as propellant gas. They may also be administered by inhalation using suitable solutions of the tiotropium salt.

DETAILED DESCRIPTION OF THE INVENTION

Surprisingly, an unexpectedly beneficial therapeutic effect, particularly a synergistic effect can be observed in the treatment of inflammatory or obstructive respiratory complaints if one or more, preferably one, tiotropium salt 1 is used in conjunction with pharmacologically acceptable salts of a betamimetic of formula 2' wherein the groups $R^1$, $R^2$, $R^3$ and $R^4$ may be defined as hereinafter.

This significantly reduces undesirable side effects, for example, which are frequently observed when β-mimetics are administered to humans. Examples of central side effects of β-mimetics include, for example, general malaise, agitation, insomnia, anxiety, trembling fingers, sweating and headaches.

Accordingly, the present invention relates to combinations of pharmaceutical compositions characterised in that that contain one or more, preferably one, tiotropium salt 1 in combination with a pharmacologically acceptable salt of a compound of formula 2' wherein
$R^1$ and $R^2$ which may be identical or different denote hydrogen or $C_1$-$C_4$-alkyl;

$R^3$ and $R^4$ which may be identical or different denote hydrogen, $C_1$-$C_4$-alkyl, —O—$C_1$-$C_4$-alkyl, —$C_1$-$C_4$-alkylene-O—$C_1$-$C_4$-alkyl or $R^3$ and $R^4$ together denote one of the bridging groups —$C_1$-$C_4$-alkylene- or —O—$C_1$-$C_4$-alkylene-O—.

Preferably in the combinations according to the invention salts of the compounds of formula 2' are used wherein $R^1$ and $R^2$ which may be identical or different denote hydrogen, methyl or ethyl;

$R^3$ and $R^4$ which may be identical or different denote hydrogen, methyl, ethyl, propyl, butyl, methoxy, ethoxy, methyoxymethyl, or methoxyethyl, or $R^3$ and $R^4$ together denote one of the bridging groups propylene, butylene, —O-ethylene-O— or —O-propylene-O—.

More preferably in the combinations according to the invention salts of the compounds of formula 2' are used wherein $R^1$ and $R^2$ which may be identical or different denote hydrogen or ethyl, preferably hydrogen;

$R^3$ and $R^4$ which may be identical or different denote hydrogen, methyl, ethyl, propyl, butyl or methyoxymethyl or $R^3$ and $R^4$ together denote one of the bridging groups butylene or —O-ethylene-O—.

Particularly preferably according to the invention, in the combinations according to the invention salts of the compounds of formula 2' are used wherein a) $R^1$ and $R^2$ denote hydrogen and $R^3$ and $R^4$ denote ethyl; or
b) $R^1$ and $R^2$ denote hydrogen and $R^3$ and $R^4$ denote methyl; or
c) $R^1$ and $R^2$ denote ethyl and $R^3$ and $R^4$ denote hydrogen; or
d) $R^1$ and $R^2$ denote hydrogen and $R^3$ and $R^4$ together denote butylene; or
e) $R^1$ and $R^2$ denote hydrogen and $R^3$ and $R^4$ together denote —O-ethylene-O—; or
f) $R^1$ and $R^2$ denote hydrogen and $R^3$ and $R^4$ denote tert.-butyl or
g) $R^1$ and $R^2$ denote hydrogen and $R^3$ and $R^4$ denote iso-propyl; or
h) $R^1$ and $R^2$ denote hydrogen and $R^3$ and $R^4$ denote methoxymethyl.

Of the compounds mentioned above, the structure defined under a) wherein $R^1$ and $R^2$ denote hydrogen and $R^3$ and $R^4$ denote ethyl is of outstanding importance in the pharmaceutical combinations according to the invention. The acid addition salts of this compound are hereinafter also referred to as compounds 2a, while any reference to the free base of this compound is characterised by the name 2a' according to the following formula

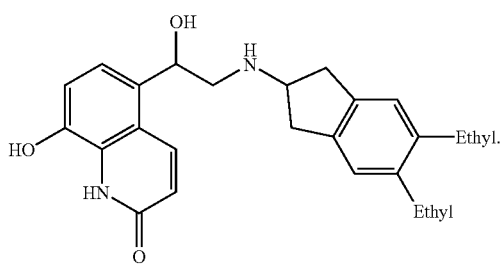

2a'

The salts 2 of the compounds of formula 2' may be used in the pharmaceutical combinations according to the invention in the form of their racemates, enantiomers or mixtures thereof. The separation of enantiomers from the racemates may be carried out using methods known in the art (e.g. by chromatography on chiral phases, etc.). If the salts of the compounds of formula 2' are used in the form of their enantiomers, the enantiomers in R configuration at the C—OH— group are particularly preferred.

The alkyl groups used, unless otherwise stated, are branched and unbranched alkyl groups having 1 to 4 carbon atoms. Examples include: methyl, ethyl, propyl or butyl. The groups methyl, ethyl, propyl or butyl may optionally also be referred to by the abbreviations Me, Et, Prop or Bu. Unless otherwise stated, the definitions propyl and butyl also include all possible isomeric forms of the groups in question. Thus, for example, propyl includes n-propyl and iso-propyl, butyl includes iso-butyl, sec. butyl and tert.-butyl, etc.

The alkylene groups used, unless otherwise stated, are branched and unbranched double-bonded alkyl bridges with 1 to 4 carbon atoms. Examples include: methylene, ethylene, propylene or butylene.

The alkyloxy groups (also referred to as —O—$C_1$-$C_4$-alkyl groups) used, unless otherwise stated, are branched and unbranched alkyl groups having 1 to 4 carbon atoms which are linked via an oxygen atom. The following may be mentioned, for example: methyloxy, ethyloxy, propyloxy or butyloxy. The groups methyloxy, ethyloxy, propyloxy or butyloxy may optionally also be referred to by the abbreviations MeO, EtO, PropO or BuO. Unless otherwise stated, the definitions propyloxy and butyloxy also include all possible isomeric forms of the groups in question. Thus, for example, propyloxy includes n-propyloxy and iso-propyloxy, butyloxy includes iso-butyloxy, sec. butyloxy and tert.-butyloxy, etc. The word alkoxy may also possibly be used within the scope of the present invention instead of the word alkyloxy. The groups methyloxy, ethyloxy, propyloxy or butyloxy may optionally also be referred to as methoxy, ethoxy, propoxy or butoxy.

The term alkylene-alkyloxy groups, unless otherwise stated, denotes branched and unbranched alkyl bridges having 1 to 4 carbon atoms which are mono-, di- or trisubstituted, preferably monosubstituted by an alkyloxy group.

Within the scope of the present invention any reference to compounds 2 is to be understood as being a reference to physiologically acceptable acid addition salts. By physiologically acceptable acid addition salts 2 are meant according to the invention pharmaceutically acceptable salts which are selected from the salts of hydrochloric acid, hydrobromic acid, sulphuric acid, phosphoric acid, methanesulphonic acid, acetic acid, fumaric acid, succinic acid, lactic acid, citric acid, tartaric acid or maleic acid. If desired, mixtures of the abovementioned acids may be used to prepare the salts 2.

According to the invention the salts 2 are preferably selected from among the hydrochloride, hydrobromide, sulphate, phosphate, fumarate, methanesulphonate and maleate. Particularly preferably, the salts 2 in the case of the compound 2a' are selected from the hydrochloride and maleate, of which the maleate is particularly preferred.

If, within the scope of the present invention, there is a reference to compounds of formula 2' which are not in the salt form, this is indicated by the designation 2', whereas a reference to 2 should be regarded as a reference to the acid addition salts of a compound of formula 2'. The compound of formula 2' and 2 and processes for the preparation thereof are known from WO 00/75114, to which reference is hereby made.

The term tiotropium within the scope of the present invention is to be regarded as a reference to the free cation (1')

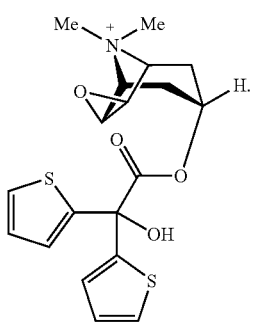

By the tiotropium salts 1 which may be used within the scope of the present invention are meant the compounds which contain, in addition to tiotropium as counter-ion (anion), chloride, bromide, iodide, methanesulphonate, para-toluenesulphonate or methylsulphate. Within the scope of the present invention, the methanesulphonate, chloride, bromide and iodide are preferred of all the tiotropium salts 1, the methanesulphonate and bromide being of particular importance. Of outstanding importance according to the invention is tiotropium bromide. The tiotropium salts 1 may optionally be used in the form of the solvates and hydrates thereof. Particularly preferably, the hydrates are used. Of all the hydrates of the tiotropium salts 1 which may be used according to the invention it is particularly preferable within the scope of the present invention to use the crystalline tiotropium bromide monohydrate described in WO 02/30928. Reference is hereby made to the entire contents of this International Patent Application. This crystalline tiotropium bromide monohydrate is characterised by an endothermic maximum at 230±5° C. at a heating rate of 10K/min, when thermally analysed by DSC. It is also characterised in that in the IR spectrum it has bands inter alia at wavelengths 3570, 3410, 3105, 1730, 1260, 1035 and 720 cm$^{-1}$. Finally, this crystalline tiotropium bromide monohydrate has a simple monoclinic cell with the following dimensions: a=18.0774 Å, b=11.9711 Å, c=9.9321 Å, β=102.691°, V=2096.96 Å$^3$ as determined by monocrystalline X-ray structural analysis.

The active substance combinations according to the invention are surprisingly characterised both by a rapid onset of activity and by their long-lasting effect. This is very important to the patient as on the one hand they will rapidly experience an improvement in their condition after taking the combination and on the other hand because of the long-lasting effect it is sufficient to take the drug once a day.

The abovementioned effects are observed both when the two active substances are taken simultaneously in a single active substance formulation and when they are administered successively in separate formulations. It is preferable according to the invention to administer the two active substance ingredients simultaneously in a single formulation.

In one aspect the present invention relates to a pharmaceutical composition which contains one or more tiotropium salts 1 and salts 2 of a compound of formula 2' optionally in the form of their solvates or hydrates. The active substances may either be combined in a single preparation or contained in two separate formulations. Pharmaceutical compositions which contain the active substances 1 and 2 in a single preparation are preferred according to the invention.

In another aspect the present invention relates to a pharmaceutical composition which contains, in addition to therapeutically effective quantities of 1 and 2, a pharmaceutically acceptable excipient. In one aspect the present invention relates to a pharmaceutical composition which does not contain any pharmaceutically acceptable excipient in addition to therapeutically effective quantities of 1 and 2.

The present invention also relates to the use of 1 and 2 for preparing a pharmaceutical composition containing therapeutically effective quantities of 1 and 2 for treating inflammatory or obstructive diseases of the respiratory tract, particularly asthma and/or COPD, by simultaneous or successive administration.

The present invention is also directed to the simultaneous or successive use of therapeutically effective doses of the combination of the above pharmaceutical compositions 1 and 2 for treating inflammatory or obstructive diseases of the respiratory tract, particularly asthma or COPD.

The proportions in which the two active substances 1 and 2 may be used in the active substance combinations according to the invention are variable. Active substances 1 and 2 may possibly be present in the form of their solvates or hydrates. Depending on the choice of the salts 1 and 2, the weight ratios which may be used within the scope of the present invention vary on the basis of the different molecular weights of the various salt forms. The proportions by weight specified below were therefore based on tiotropium 1' and the free bases 2'.

The active substance combinations according to the invention may contain 1' and 2' in proportions by weight in a range from 1:300 to 30:1, preferably from 1:230 to 20:1, more preferably from 1:150 to 1:1, still more preferably from 1:50 to 5:1, more preferably from 1:35 to 2:1.

For example, without restricting the scope of the invention thereto, preferred combinations of 1 and 2 may contain tiotropium 1' and the particularly preferred compound 2a' in the following weight ratios: 1:40; 1:39; 1:38; 1:37; 1:36; 1:35; 1:34; 1:33; 1:32; 1:31; 1:30; 1:29; 1:28; 1:27; 1:26; 1:25; 1:24; 1:23; 1:22; 1:21; 1:20; 1:19; 1:18; 1:17; 1:16; 1:15; 1:14; 1:13; 1:12; 1:11; 1:10; 1:9; 1:8; 1:7; 1:6; 1:5; 1:4; 1:3; 1:2; 1:1; 2:1; 3:1; 4:1; 5:1.

The pharmaceutical compositions according to the invention containing the combinations of 1 and 2 are usually administered by giving tiotropium 1' and 2' together in doses from 0.01 to 10000 μg, preferably from 0.1 to 2000 μg, more preferably from 10 to 1000 μg, still more preferably from 15 to 500 μg per single dose.

For example, combinations of 1 and 2 according to the invention contain an amount of tiotropium 1' and the particularly preferred compound 2a' such that the total dose per single dose is 15 μg, 20 μg, 25 μg, 30 μg, 35 μg, 45 μg, 50 μg, 55 μg, 60 μg, 65 μg, 70 μg 75 μg, 80 μg, 85 μg, 90 μg, 95 μg, 100 μg, 105 μg, 110 μg, 115 μg, 120 μg, 125 μg, 130 μg, 135 μg, 140 μg, 145 μg, 150 μg, 155 μg, 160 μg, 165 μg, 170 μg, 175 μg, 180 μg, 185 μg, 190 μg, 195 μg, 200 μg, 205 μg, 210 μg, 215 μg, 220 μg, 225 μg, 230 μg, 235 μg, 240 μg, 245 μg, 250 μg, 255 μg, 260 μg, 265 μg, 270 μg, 275 μg, 280 μg, 285 μg, 290 μg, 295 μg, 300 μg, 305 μg, 310 μg, 315 μg, 320 μg, 325 μg, 330 μg, 335 μg, 340 μg, 345 μg, 350 μg, 355 μg, 360 μg, 365 μg, 370 μg, 375 μg, 380 μg, 385 μg, 390 μg, 395 μg, 400 μg, 405 μg, 410 μg, 415 μg, 420 μg, 425 μg, 430 μg, 435 μg, 440 μg, 445 μg, 450 μg, 455 μg, 460 μg, 465 μg, 470 µg, 475 µg, 480 µg, 485 µg, 490 µg, 495 µg, 500 µg, 505 µg, or the like. In these dosage ranges the active substances 1' and 2a' are present in the ratios by weight described above.

For example, without restricting the scope of the invention thereto, the combinations of 1 and 2 according to the invention may contain the following amounts of tiotropium 1' and 2a' for example: 5 µg of 1' and 12.5 µg of 2a', 5 µg of 1' and 25 µg of 2a', 5 µg of 1' and 50 µg of 2a', 5 µg of 1' and 75 µg of 2a', 5 µg of 1' and 100 µg of 2a', 5 µg of 1' and 200 µg of 2a', 10 µg of 1' and 12.5 µg of 2a', 10 µg of 1' and 25 µg of 2a', 10 µg of 1' and 50 µg of 2a', 10 µg of 1' and 75 µg of 2a', 10 µg of 1' and 100 µg of 2a', 10 µg of 1' and 200 µg of 2a', 18 µg of 1' and 12.5 µg of 2a', 18 µg of 1' and 25 µg of 2a', 18 µg of 1' and 50 µg of 2a', 18 µg of 1' and 75 µg of 2a', 18 µg of 1' and 100 µg of 2a', 18 µg of 1' and 200 µg of 2a', 20 µg of 1' and 12.5 µg of 2a', 20 µg of 1' and 25 µg of 2a', 20 µg of 1' and 50 µg of 2a', 20 µg of 1' and 75 µg of 2a', 20 µg of 1' and 100 µg of 2a', 20 µg of 1' and 200 µg of 2a', 36 µg of 1' and 12.5 µg of 2a', 36 µg of 1' and 25 µg of 2a', 36 µg of 1' and 50 µg of 2a', 36 µg of 1' and 75 µg of 2a', 36 µg of 1' and 100 µg of 2a', 36 µg of 1' and 200 µg of 2a', 40 µg of 1' and 12.5 µg of 2a', 40 µg of 1' and 25 µg of 2a', 40 µg of 1' and 50 µg of 2a', 40 µg of 1' and 75 µg of 2a', 40 µg of 1' and 100 µg of 2a' or 40 µg of 1' and 200 µg of 2a'.

If the active substance combination in which 1 denotes tiotropium bromide and 2 denotes the particularly preferred salt 2a, the maleate salt of the compound 2a', is used as the preferred combination of 1 and 2 according to the invention, the quantities of active substance 1' and 2a' administered per single dose mentioned by way of example correspond to the following quantities of 1 and 2a administered per single dose: 6 µg of 1 and 16.2 µg of 2a, 6 µg of 1 and 32.4 µg of 2a, 6 µg of 1 and 64.8 µg of 2a, 6 µg of 1 and 97.2 µg of 2a, 6 µg of 1 and 129.6 µg of 2a, 6 µg of 1 and 259.2 µg of 2a, 12 µg of 1 and 16.2 µg of 2a, 12 µg of 1 and 32.4 µg of 2a, 12 µg of 1 and 64.8 µg of 2a, 12 µg of 1 and 97.2 µg of 2a, 12 µg of 1 and 129.6 µg of 2a, 12 µg of 1 and 259.2 µg of 2a, 21.7 µg of 1 and 16.2 µg of 2a, 21.7 µg of 1 and 32.4 µg of 2a, 21.7 µg of 1 and 64.8 µg of 2a, 21.7 µg of 1 and 97.2 µg of 2a, 21.7 µg of 1 and 129.6 µg of 2a, 21.7 µg of 1 and 259.2 µg of 2a, 24.1 µg of 1 and 12.5 µg of 2a, 24.1 µg of 1 and 32.4 µg of 2a, 24.1 µg of 1 and 64.8 µg of 2a, 24.1 µg of 1 and 97.2 µg of 2a, 24.1 µg of 1 and 129.6 µg of 2a, 24.1 µg of 1 and 259.2 µg of 2a, 43.3 µg of 1 and 16.2 µg of 2a, 43.3 µg of 1 and 32.4 µg of 2a, 43.3 µg of 1 and 64.8 µg of 2a, 43.3 µg of 1 and 97.2 µg of 2a, 43.3 µg of 1 and 129.6 µg of 2a, 43.3 µg of 1 and 259.2 µg of 2a, 48.1 µg of 1 and 16.2 µg of 2a, 48.1 µg of 1 and 32.4 µg of 2a, 48.1 µg of 1 and 64.8 µg of 2a, 48.1 µg of 1 and 97.2 µg of 2a or 48.1 µg of 1 and 129.6 µg of 2a, 48.1 µg of 1 and 259.2 µg of 2a.

If the active substance combination of 1 and 2 used according to the invention is the combination in which 1 denotes the crystalline tiotropium bromide monohydrate which is particularly preferred according to the invention and 2 denotes the particularly preferred salt 2a, the maleate salt of the compound 2a', the quantities of active substance 1' and 2a' administered per single dose mentioned by way of example correspond to the following quantities of 1 and 2a administered per single dose: 6.2 µg of 1 and 16.2 µg of 2a, 6.2 µg of 1 and 32.4 µg of 2a, 6.2 µg of 1 and 64.8 µg of 2a, 6.2 µg of 1 and 97.2 µg of 2a, 6.2 µg of 1 and 129.6 µg of 2a, 6.2 µg of 1 and 259.2 µg of 2a, 12.5 µg of 1 and 16.2 µg of 2a, 12.5 µg of 1 and 32.4 µg of 2a, 12.5 µg of 1 and 64.8 µg of 2a, 12.5 µg of 1 and 97.2 µg of 2a, 12.5 µg of 1 and 129.6 µg of 2a, 12.5 µg of 1 and 259.2 µg of 2a, 22.5 µg of 1 and 16.2 µg of 2a, 22.5 µg of 1 and 32.4 µg of 2a, 22.5 µg of 1 and 64.8 µg of 2a, 22.5 µg of 1 and 97.2 µg of 2a, 22.5 µg of 1 and 129.6 µg of 2a, 22.5 µg of 1 and 259.2 µg of 2a, 25 µg of 1 and 12.5 µg of 2a, 25 µg of 1 and 32.4 µg of 2a, 25 µg of 1 and 64.8 µg of 2a, 25 µg of 1 and 97.2 µg of 2a, 25 µg of 1 and 129.6 µg of 2a, 25 µg of 1 and 259.2 µg of 2a, 45 µg of 1 and 16.2 µg of 2a, 45 µg of 1 and 32.4 µg of 2a, 45 µg of 1 and 64.8 µg of 2a, 45 µg of 1 and 97.2 µg of 2a, 45 µg of 1 and 129.6 µg of 2a, 45 µg of 1 and 259.2 µg of 2a, 50 µg of 1 and 16.2 µg of 2a, 50 µg of 1 and 32.4 µg of 2a, 500 µg of 1 and 64.8 µg of 2a, 50 µg of 1 and 97.2 µg of 2a or 50 µg of 1 and 129.6 µg of 2a, 50 µg of 1 and 259.2 µg of 2a.

The active substance combinations of 1 and 2 according to the invention are preferably administered by inhalation or by nasal application. For this purpose, ingredients 1 and 2 have to be made available in inhalable forms. Inhalable preparations include, in particular, inhalable powders. Inhalable powders according to the invention containing the combination of active substances 1 and 2 may consist of the active substances on their own or of a mixture of the active substances with physiologically acceptable excipients. The preparations according to the invention may contain the combination of active substances 1 and 2 either together in one formulation or in two separate formulations. These formulations which may be used within the scope of the present invention are described in more detail in the next part of the specification.

A) Inhalable Powder Containing the Combinations of Active Substances 1 and 2 According to the Invention:

The inhalable powders according to the invention may contain 1 and 2 either on their own or in admixture with suitable physiologically acceptable excipients.

If the active substances 1 and 2 are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose, trehalose), oligo- and polysaccharides (e.g. dextrane), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 µm, preferably between 10 and 150 µm, most preferably between 15 and 80 µm. It may sometimes seem appropriate to add finer excipient fractions with an average particle size of 1 to 9 µm to the excipients mentioned above. These finer excipients are also selected from the group of possible excipients listed hereinbefore. In particularly preferred inhalable powders the excipient is characterised by an average particle size of 12 to 35 µm, more preferably from 13 to 30 µm. Also particularly preferred are inhalable powders in which the 10% fine content is about 1 to 4 µm, preferably about 1.5 to 3 µm.

By the average particle size is meant here the 50% value of the volume distribution measured using a laser diffractometer by the dry dispersion method. Analogously, the 10% fine content in this instance refers to the 10% value of the volume distribution measured using a laser diffractometer.

Preferably, excipients of high crystallinity are used for the powder formulations according to the invention. This crystallinity can be assessed by means of the enthalpy released as the excipient is dissolved (solution enthalpy). In the case of the excipient lactose monohydrate, which is most preferably used acording to the invention, it is preferable to use lactose which is characterised by a solution enthalpy of $\geqq 45$ J/g, preferably $\geqq 50$ J/g, particularly preferably $\geqq 52$ J/g.

Finally, in order to prepare the inhalable powders according to the invention, micronised active substance 1 and 2, preferably with an average particle size of 0.5 to 10 μm, more preferably from 1 to 5 μm, are added to the excipient mixture.

If the active substance 1 used is the crystalline tiotropium bromide monohydrate disclosed by WO 02/30928 which is particularly preferred according to the invention the following procedure has proved particularly suitable for micronising this crystalline active substance modification. The process may be carried out using conventional mills. Preferably, the micronisation is carried out with the exclusion of moisture, more preferably, using a corresponding inert gas such as nitrogen, for example. It has proved particularly preferable to use air jet mills in which the material is comminuted by the impact of the particles on one another and on the walls of the grinding container.

According to the invention, nitrogen is preferably used as the grinding gas. The material for grinding is conveyed by the grinding gas under specific pressures (grinding pressure). Within the scope of the present invention, the grinding pressure is usually set to a value between about 2 and 8 bar, preferably between about 3 and 7 bar, most preferably between about 3.5 and 6.5 bar. The material for grinding is fed into the air jet mill by means of the feed gas under specific pressures (feed pressure). Within the scope of the present invention a feed pressure of between about 2 and 8 bar, preferably between about 3 and 7 bar and most preferably between about 3.5 and 6 bar has proved satisfactory. The feed gas used is also preferably an inert gas, most preferably nitrogen again. The material to be ground (crystalline tiotropium bromide monohydrate) may be fed in at a rate of about 5-35 g/min, preferably at about 10-30 g/min.

For example, without restricting the subject of the invention thereto, the following apparatus has proved suitable as a possible embodiment of an air jet mill: a 2-inch Microniser with grinding ring, 0.8 mm bore, made by Messrs Sturtevant Inc., 348 Circuit Street, Hanover, Mass. 02239, USA. Using this apparatus, the grinding process is preferably carried out with the following grinding parameters: grinding pressure: about 4.5-6.5 bar; feed pressure: about 4.5-6.5 bar; supply of grinding material: about 17-21 g/min.

The ground material thus obtained is then further processed under the following specific conditions. The micronisate is exposed to water vapour at a relative humidity of at least 40% at a temperature of 15-40° C., preferably 20-35° C., most preferably 25-30° C. Preferably, the humidity is set to a value of 50-95% r.h., preferably 60-90% r.h., most preferably 70-80% r.h. By relative humidity (r.h.) is meant the quotient of the partial steam pressure and the steam pressure of the water at the temperature in question. Preferably, the micronisate obtained from the grinding process described above is subjected to the chamber conditions mentioned above for a period of at least 6 hours. Preferably, however, the micronisate is subjected to the chamber conditions mentioned above for about 12 to 48 hours, preferably about 18 to 36 hours, more preferably about 20 to 28 hours.

The micronisate of tiotropium bromide obtainable by the above method has a characteristic particle size of between 1.0 μm and 3.5 μm, preferably between 1.1 μm and 3.3 μm, most preferably between 1.2 μm and 3.0 μm and $Q_{(5.8)}$ of more than 60%, preferably more than 70%, most preferably more than 80%. The characteristic value $Q_{(5.8)}$ indicates the quantity of particles below 5.8 μm, based on the volume distribution of the particles. The particle sizes were determined within the scope of the present invention by laser diffraction (Fraunhofer diffraction). More detailed information on this subject can be found in the experimental descriptions of the invention.

Also characteristic of the tiotropium micronisate according to the invention which was prepared by the above process are Specific Surface Area values in the range between 2 m²/g and 5 m²/g, more particularly between 2.5 m²/g and 4.5 m²/g and most outstandingly between 3.0 m²/g and 4.0 m²/g.

After the starting materials have been weighed in the inhalable powders are prepared from the excipient and the active substances 1 and 2 using methods known in the art. Reference may be made to the disclosure of WO 02/30390, for example.

The inhalable powders according to the invention may be prepared and administered either in the form of a single powder mixture which contains both 1 and 2 or in the form of separate inhalable powders which contain only 1 or 2.

The inhalable powders according to the invention may be administered using inhalers known from the prior art.

Inhalable powders according to the invention which contain a physiologically acceptable excipient in addition to 1 and 2 may be administered, for example, by means of inhalers which deliver a single dose from a supply using a measuring chamber as described in U.S. Pat. No. 4,570,630A, or by other means as described in DE 36 25 685 A. Preferably, the inhalable powders according to the invention which contain physiologically acceptable excipient in addition to 1 and 2 are packed into capsules (to produce so-called inhalettes) which are used in inhalers as described, for example, in WO 94/28958.

A particularly preferred inhaler for administering the pharmaceutical combination according to the invention in inhalettes is shown in FIG. 1.

This inhaler (Handyhaler) for inhaling powdered pharmaceutical compositions from capsules is characterised by a housing 1 containing two windows 2, a deck 3 in which there are air inlet ports and which is provided with a screen 5 secured via a screen housing 4, an inhalation chamber 6 connected to the deck 3 on which there is a push button 8 provided with two sharpened pins 7 and movable counter to a spring 8, and a mouthpiece 12 which is connected to the housing 1, the deck 3 and a cover 11 via a spindle 10 to enable it to be flipped open or shut, and air holes 13 for adjusting the flow resistance.

For administering the inhalable powders according to the invention containing 1 and 2 using powder-filled capsules it is particularly preferred to use capsules the material of which is selected from among the synthetic plastics, most preferably selected from among polyethylene, polycarbonate, polyester, polypropylene and polyethylene terephthalate. Particularly preferred synthetic plastic materials are polyethylene, polycarbonate or polyethylene terephthalate. If polyethylene is used as one of the capsule materials which is particularly preferred according to the invention, it is preferable to use polyethylene with a density of between 900 and 1000 kg/m³, preferably 940-980 kg/m³, more preferably about 960-970 kg/m³ (high density polyethylene).

The synthetic plastics according to the invention may be processed in various ways using manufacturing methods known in the art. Injection moulding of the plastics is preferred according to the invention. Injection moulding without the use of mould release agents is particularly preferred. This method of production is well defined and is characterised by being particularly reproducible.

In another aspect the present invention relates to the abovementioned capsules which contain the abovementioned inhalable powders containing 1 and 2 according to the invention. If the inhalable powders according to the invention are intended to be packed into capsules (inhalettes) for the preferred use described above, fill amounts of from 1 to 30 mg, preferably from 3 to 20 mg, preferably 5 to 10 mg of inhalable powder per capsule are recommended. These contain, according to the invention, either together or separately, the abovementioned dosages of 1 and 2 per single dose. As already mentioned, the present invention also relates to a kit consisting of two capsules each of which contains the active substances 1 and 2 optionally combined with one of the abovementioned physiologically acceptable excipients.

The present invention also relates to an inhalation kit consisting of one or more of the above capsules characterised by a content of inhalable powder containing 1 and 2 according to the invention in conjunction with the inhaler according to FIG. 1.

The present invention also relates to the use of the abovementioned capsules characterised by a content of inhalable powder containing 1 and 2 according to the invention, for preparing a pharmaceutical composition for treating respiratory complaints, especially for treating COPD and/or asthma.

Filled capsules which contain the inhalable powders according to the invention are produced by methods known in the art, by filling the empty capsules with the inhalable powders according to the invention.

B) Propellant Gas-Driven Inhalation Aerosols Containing the Combinations of Active Substances 1 and 2:

Inhalation aerosols containing propellant gas according to the invention may contain substances 1 and 2 dissolved in the propellant gas or in dispersed form. 1 and 2 may be present in separate formulations or in a single preparation, in which 1 and 2 are either each dissolved, dispersed or only one or two of the components is or are dissolved and the other or others is or are dispersed. The propellant gases which may be used to prepare the inhalation aerosols according to the invention are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The propellant gases mentioned above may be used on their own or in mixtures thereof. Particularly preferred propellant gases are halogenated alkane derivatives selected from TG134a, TG227 and mixtures thereof.

The propellant-driven inhalation aerosols according to the invention may also contain other ingredients such as co-solvents, stabilisers, surfactants, antioxidants, lubricants and pH adjusters. All these ingredients are known in the art.

The inhalation aerosols containing propellant gas according to the invention may contain up to 5 wt.-% of active substance 1 and/or 2. Aerosols according to the invention contain, for example, 0.002 to 5 wt.-%, 0.01 to 3 wt.-%, 0.015 to 2 wt.-%, 0.1 to 2 wt.-%, 0.5 to 2 wt.-% or 0.5 to 1 wt.-% of active substance 1 and/or 2.

If the active substances 1 and/or 2 are present in dispersed form, the particles of active substance preferably have an average particle size of up to 10 µm, preferably from 0.1 to 5 µm, more preferably from 1 to 5 µm. If 1 is to be used in the form of its crystalline tiotropium bromide monohydrate this may optionally be used in the form of the micronisate described in more detail in the previous section.

The propellant-driven inhalation aerosols according to the invention mentioned above may be administered using inhalers known in the art (MDIs=metered dose inhalers). Accordingly, in another aspect, the present invention relates to pharmaceutical compositions in the form of propellant-driven aerosols as hereinbefore described combined with one or more inhalers suitable for administering these aerosols. In addition, the present invention relates to inhalers which are characterised in that they contain the propellant gas-containing aerosols described above according to the invention.

The present invention also relates to cartridges which are fitted with a suitable valve and can be used in a suitable inhaler and which contain one of the above-mentioned propellant gas-containing inhalation aerosols according to the invention. Suitable cartridges and methods of filling these cartridges with the inhalable aerosols containing propellant gas according to the invention are known from the prior art.

C) Propellant-Free Inhalable Solutions or Suspensions Containing the Combinations of Active Substances 1 and 2 According to the Invention:

It is particularly preferred to use the active substance combination according to the invention in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is up to 70 percent by volume, more particularly up to 60 percent by volume and most preferably up to 30 percent by volume. The remainder of the volume is made up of water. The solutions or suspensions containing 1 and 2, separately or together, are adjusted to a pH of 2 to 7, preferably 2 to 5, using suitable acids. The pH may be adjusted using acids selected from inorganic or organic acids. Examples of suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

According to the invention, the addition of editic acid (EDTA) or one of the known salts thereof, sodium edetate, as stabiliser or complexing agent is unnecessary in the present formulation. Other embodiments may contain this compound or these compounds. In a preferred embodiment the content based on sodium edetate is less than 100 mg/100 ml, preferably less than 50 mg/100 ml, more preferably less than 20 mg/100 ml. Generally, inhalable solutions in which the content of sodium edetate is from 0 to 10 mg/100 ml are preferred.

Co-solvents and/or other excipients may be added to the propellant-free inhalable solutions according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include physiologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body.

Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 ml, more preferably between 5 and 20 mg/100 ml.

Preferred formulations contain, in addition to the solvent water and the combination of active substances 1 and 2, only benzalkonium chloride and sodium edetate. In another preferred embodiment, no sodium edetate is present.

The propellant-free inhalable solutions according to the invention are administered in particular using inhalers of the kind which are capable of nebulising a small amount of a liquid formulation in the required therapeutic dose within a few seconds to produce an aerosol suitable for therapeutic inhalation. Within the scope of the present invention, preferred nebulisers are those in which a quantity of less than 100 μL, preferably less than 50 μL, more preferably between 20 and 30 μL of active substance solution can be nebulised in preferably one spray action to form an aerosol with an average particle size of less than 20 μm, preferably less than 10 μm, in such a way that the inhalable part of the aerosol corresponds to the therapeutically effective quantity.

An apparatus of this kind for propellant-free delivery of a metered quantity of a liquid pharmaceutical composition for inhalation is described for example in International Patent Application WO 91/14468 and also in WO 97/12687 (cf. in particular FIGS. 6a and 6b). The nebulisers (devices) described therein are known by the name Respimat®.

This nebuliser (Respimat®) can advantageously be used to produce the inhalable aerosols according to the invention containing the combination of active substances 1 and 2. Because of its cylindrical shape and handy size of less than 9 to 15 cm long and 2 to 4 cm wide, this device can be carried at all times by the patient. The nebuliser sprays a defined volume of pharmaceutical formulation using high pressures through small nozzles so as to produce inhalable aerosols.

The preferred atomiser essentially consists of an upper housing part, a pump housing, a nozzle, a locking mechanism, a spring housing, a spring and a storage container, characterised by
    a pump housing which is secured in the upper housing part and which comprises at one end a nozzle body with the nozzle or nozzle arrangement,
    a hollow plunger with valve body,
    a power takeoff flange in which the hollow plunger is secured and which is located in the upper housing part,
    a locking mechanism situated in the upper housing part,
    a spring housing with the spring contained therein, which is rotatably mounted on the upper housing part by means of a rotary bearing,
    a lower housing part which is fitted onto the spring housing in the axial direction.

The hollow plunger with valve body corresponds to a device disclosed in WO 97/12687. It projects partially into the cylinder of the pump housing and is axially movable within the cylinder. Reference is made in particular to FIGS. 1 to 4, especially FIG. 3, and the relevant parts of the description. The hollow plunger with valve body exerts a pressure of 5 to 60 Mpa (about 50 to 600 bar), preferably 10 to 60 Mpa (about 100 to 600 bar) on the fluid, the measured amount of active substance solution, at its high pressure end at the moment when the spring is actuated. Volumes of 10 to 50 microlitres are preferred, while volumes of 10 to 20 microlitres are particularly preferred and a volume of 15 microlitres per spray is most particularly preferred.

The valve body is preferably mounted at the end of the hollow plunger facing the valve body.

The nozzle in the nozzle body is preferably microstructured, i.e. produced by microtechnology. Microstructured valve bodies are disclosed for example in WO-94/07607; reference is hereby made to the contents of this specification, particularly FIG. 1 therein and the associated description.

The nozzle body consists for example of two sheets of glass and/or silicon firmly joined together, at least one of which has one or more microstructured channels which connect the nozzle inlet end to the nozzle outlet end. At the nozzle outlet end there is at least one round or non-round opening 2 to 10 microns deep and 5 to 15 microns wide, the depth preferably being 4.5 to 6.5 microns while the length is preferably 7 to 9 microns.

In the case of a plurality of nozzle openings, preferably two, the directions of spraying of the nozzles in the nozzle body may extend parallel to one another or may be inclined relative to one another in the direction of the nozzle opening. In a nozzle body with at least two nozzle openings at the outlet end the directions of spraying may be at an angle of 20 to 160° to one another, preferably 60 to 150°, most preferably 80 to 100°. The nozzle openings are preferably arranged at a spacing of 10 to 200 microns, more preferably at a spacing of 10 to 100 microns, most preferably 30 to 70 microns. Spacings of 50 microns are most preferred. The directions of spraying will therefore meet in the vicinity of the nozzle openings.

The liquid pharmaceutical preparation strikes the nozzle body with an entry pressure of up to 600 bar, preferably 200 to 300 bar, and is atomised into an inhalable aerosol through the nozzle openings. The preferred particle or droplet sizes of the aerosol are up to 20 microns, preferably 3 to 10 microns.

The locking mechanism contains a spring, preferably a cylindrical helical compression spring, as a store for the mechanical energy. The spring acts on the power takeoff flange as an actuating member the movement of which is determined by the position of a locking member. The travel of the power takeoff flange is precisely limited by an upper and lower stop. The spring is preferably biased, via a power step-up gear, e.g. a helical thrust gear, by an external torque which is generated when the upper housing part is rotated counter to the spring housing in the lower housing part. In this case, the upper housing part and the power takeoff flange have a single or multiple V-shaped gear.

The locking member with engaging locking surfaces is arranged in a ring around the power takeoff flange. It consists, for example, of a ring of plastic or metal which is inherently radially elastically deformable. The ring is arranged in a plane at right angles to the atomiser axis. After the biasing of the spring, the locking surfaces of the locking member move into the path of the power takeoff flange and prevent the spring from relaxing. The locking member is actuated by means of a button. The actuating button is connected or coupled to the locking member. In order to actuate the locking mechanism, the actuating button is moved parallel to the annular plane, preferably into the atomiser; this causes the deformable ring to deform in the annular plane. Details of the construction of the locking mechanism are given in WO 97/20590.

The lower housing part is pushed axially over the spring housing and covers the mounting, the drive of the spindle and the storage container for the fluid.

When the atomiser is actuated the upper housing part is rotated relative to the lower housing part, the lower housing part taking the spring housing with it. The spring is thereby compressed and biased by means of the helical thrust gear and the locking mechanism engages automatically. The angle of rotation is preferably a whole-number fraction of 360 degrees, e.g. 180 degrees. At the same time as the spring is biased, the power takeoff part in the upper housing part is moved along by a given distance, the hollow plunger is withdrawn inside the cylinder in the pump housing, as a result of which some of the fluid is sucked out of the storage container and into the high pressure chamber in front of the nozzle.

If desired, a number of exchangeable storage containers which contain the fluid to be atomised may be pushed into the atomiser one after another and used in succession. The storage container contains the aqueous aerosol preparation according to the invention.

The atomising process is initiated by pressing gently on the actuating button. As a result, the locking mechanism opens up the path for the power takeoff member. The biased spring pushes the plunger into the cylinder of the pump housing. The fluid leaves the nozzle of the atomiser in atomised form.

Further details of construction are disclosed in PCT Applications WO 97/12683 and WO 97/20590, to which reference is hereby made.

The components of the atomiser (nebuliser) are made of a material which is suitable for its purpose. The housing of the atomiser and, if its operation permits, other parts as well, are preferably made of plastics, e.g. by injection moulding. For medicinal purposes, physiologically safe materials are used.

Figure 2A:
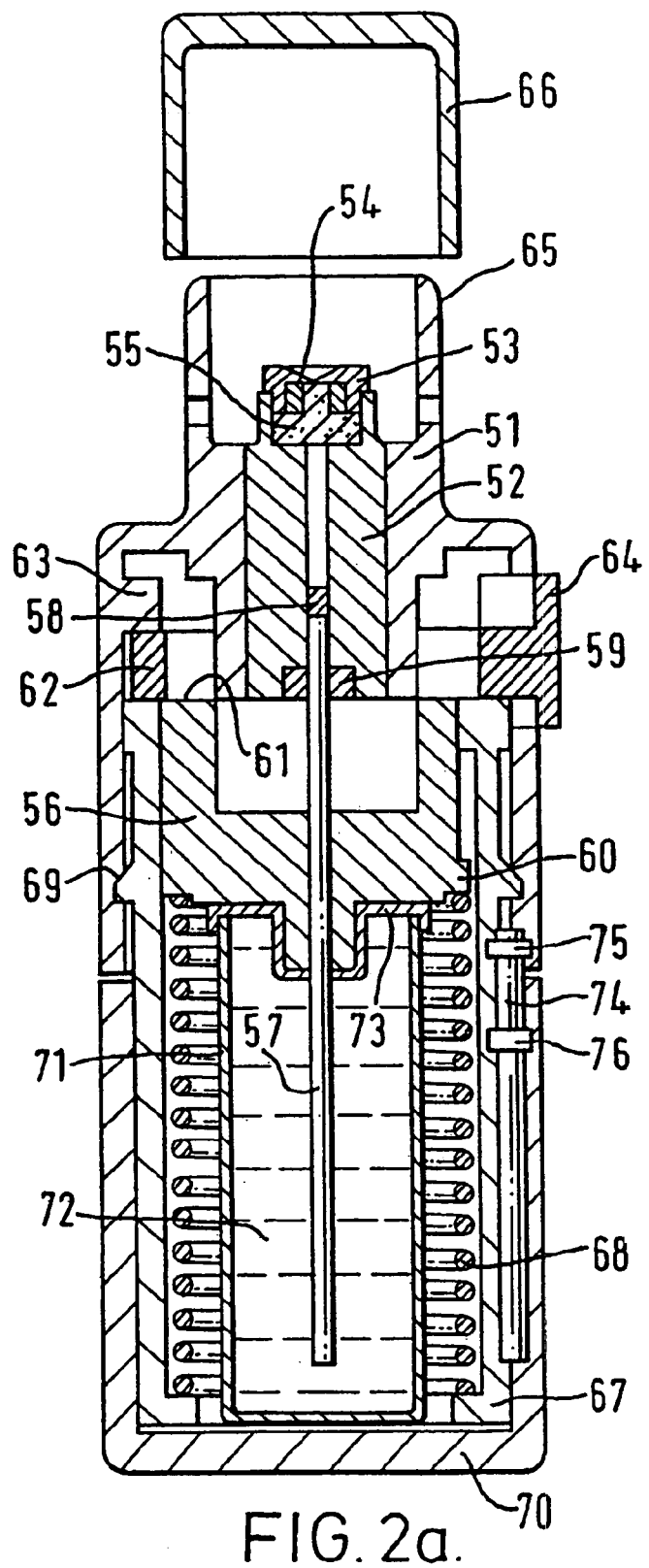

FIGS. 2a/b attached to this patent application, which are identical to FIGS. 6 a/b of WO 97/12687, show the nebuliser (Respimat®) which can advantageously be used for inhaling the aqueous aerosol preparations according to the invention.

Figure 2B:
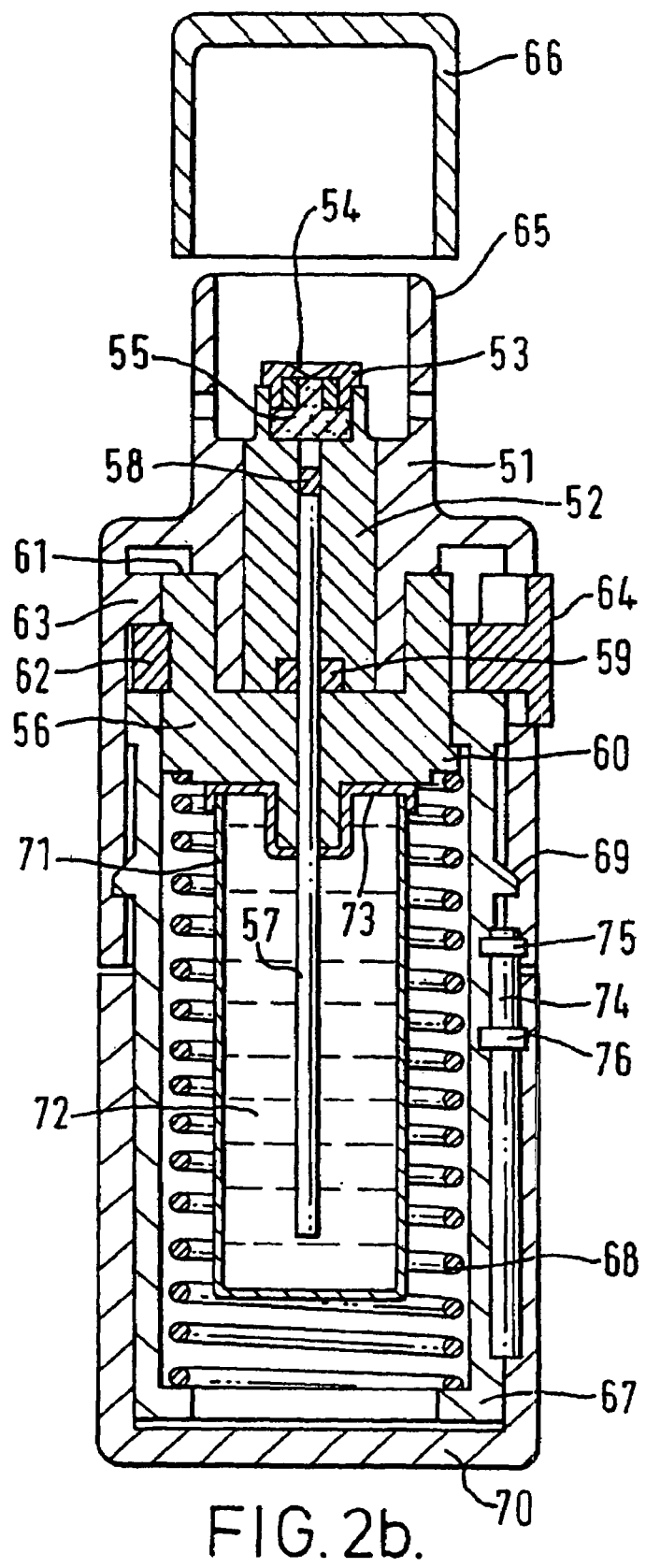

FIG. 2a shows a longitudinal section through the atomiser with the spring biased while FIG. 2b shows a longitudinal section through the atomiser with the spring relaxed.

The upper housing part (51) contains the pump housing (52) on the end of which is mounted the holder (53) for the atomiser nozzle. In the holder is the nozzle body (54) and a filter (55). The hollow plunger (57) fixed in the power takeoff flange (56) of the locking mechanism projects partially into the cylinder of the pump housing. At its end the hollow plunger carries the valve body (58). The hollow plunger is sealed off by means of the seal (59). Inside the upper housing part is the stop (60) on which the power takeoff flange abuts when the spring is relaxed. On the power takeoff flange is the stop (61) on which the power takeoff flange abuts when the spring is biased. After the biasing of the spring the locking member (62) moves between the stop (61) and a support (63) in the upper housing part. The actuating button (64) is connected to the locking member. The upper housing part ends in the mouthpiece (65) and is sealed off by means of the protective cover (66) which can be placed thereon.

The spring housing (67) with compression spring (68) is rotatably mounted on the upper housing part by means of the snap-in lugs (69) and rotary bearing. The lower housing part (70) is pushed over the spring housing. Inside the spring housing is the exchangeable storage container (71) for the fluid (72) which is to be atomised. The storage container is sealed off by the stopper (73) through which the hollow plunger projects into the storage container and is immersed at its end in the fluid (supply of active substance solution).

The spindle (74) for the mechanical counter is mounted in the covering of the spring housing. At the end of the spindle facing the upper housing part is the drive pinion (75). The slider (76) sits on the spindle.

The nebuliser described above is suitable for nebulising the aerosol preparations according to the invention to produce an aerosol suitable for inhalation.

If the formulation according to the invention is nebulised using the method described above (Respimat®) the quantity delivered should correspond to a defined quantity with a tolerance of not more than 25%, preferably 20% of this amount in at least 97%, preferably at least 98% of all operations of the inhaler (spray actuations). Preferably, between 5 and 30 mg of formulation, most preferably between 5 and 20 mg of formulation are delivered as a defined mass on each actuation.

However, the formulation according to the invention may also be nebulised by means of inhalers other than those described above, e.g. jet stream inhalers.

Accordingly, in a further aspect, the invention relates to pharmaceutical formulations in the form of propellant-free inhalable solutions or suspensions as described above combined with a device suitable for administering these formulations, preferably in conjunction with the Respimat®. Preferably, the invention relates to propellant-free inhalable solutions or suspensions characterised by the combination of active substances 1 and 2 according to the invention in conjunction with the device known by the name Respimat®. In addition, the present invention relates to the above-mentioned devices for inhalation, preferably the Respimat®, characterised in that they contain the propellant-free inhalable solutions or suspensions according to the invention as described hereinbefore.

The propellant-free inhalable solutions or suspensions according to the invention may take the form of concentrates or sterile inhalable solutions or suspensions ready for use, as well as the above-mentioned solutions and suspensions designed for use in a Respimat®. Formulations ready for use may be produced from the concentrates, for example, by the addition of isotonic saline solutions. Sterile formulations ready for use may be administered using energy-operated fixed or portable nebulisers which produce inhalable aerosols by means of ultrasound or compressed air by the Venturi principle or other principles.

Accordingly, in another aspect, the present invention relates to pharmaceutical compositions in the form of propellant-free inhalable solutions or suspensions as described hereinbefore which take the form of concentrates or sterile formulations ready for use, combined with a device suitable for administering these solutions, characterised in that the device is an energy-operated free-standing or portable nebuliser which produces inhalable aerosols by means of ultrasound or compressed air by the Venturi principle or other methods.

The Examples which follow serve to illustrate the present invention in more detail without restricting the scope of the invention to the following embodiments by way of example.

Starting Materials

I) Micronising Crystalline Tiotropium Bromide Monohydrate:

The tiotropium bromide monohydrate obtainable by the process according to WO 02/30928 is micronised with an air jet mill of the 2-inch microniser type with grinding ring, 0.8 mm bore, made by Messrs Sturtevant Inc., 348 Circuit Street, Hanover, Mass. 02239, USA. Using nitrogen as the grinding gas the following grinding parameters are set, for example:

grinding pressure: 5.5 bar; feed pressure: 5.5 bar; supply (of crystalline monohydrate) or flow speed: 19 g/min.

The ground material obtained is then spread out on sheet metal racks in a layer thickness of about 1 cm and subjected to the following climatic conditions for 24-24.5 hours: temperature: 25-30° C.; relative humidity: 70-80%.

Measuring Methods:

Determining the Particle Size of Micronised Tiotropium Monohydrate:

Measuring Equipment and Settings:

The equipment is operated according to the manufacturer's instructions.

| | |
|---|---|
| Measuring equipment: | HELOS Laser-diffraction spectrometer, (SympaTec) |
| Dispersing unit: | RODOS dry disperser with suction funnel, (SympaTec) |
| Sample quantity: | 200 mg ± 150 mg |
| Product feed: | Vibri Vibrating channel, Messrs. Sympatec |
| Frequency of vibrating channel: | rising to 100% |
| Duration of sample feed: | 15 to 25 sec. (in the case of 200 mg) |
| Focal length: | 100 mm (measuring range: 0.9–175 μm) |
| Measuring time: | about 15 s (in the case of 200 mg) |
| Cycle time: | 20 ms |
| Start/stop at: | 1% on channel 28 |
| Dispersing gas: | compressed air |
| Pressure: | 3 bar |
| Vacuum: | maximum |
| Evaluation method: | HRLD |

Sample Preparation/Product Feed:

About 200 mg of the test substance are weighed onto a piece of card.

Using another piece of card all the larger lumps are broken up. The powder is then sprinkled finely over the front half of the vibrating channel (starting about 1 cm from the front edge). After the start of the measurement the frequency of the vibrating channel is varied so that the sample is fed in as continuously as possible. However, the quantity of product should not be too great either, so as to ensure adequate dispersal.

II) Determining the Particle Size of the Excipient (in This Case Lactose):

Measuring Equipment and Settings:

The equipment is operated according to the manufacturer's instructions.

| | |
|---|---|
| Measuring equipment: | HELOS Laser-diffraction spectrometer, (SympaTec) |
| Dispersing unit: | RODOS dry disperser with suction funnel, (SympaTec) |
| Sample quantity: | 200 mg ± 100 mg |
| Product feed: | Vibri Vibrating channel, Messrs. Sympatec |
| Frequency of vibrating channel: | 100% rising |
| Focal length: | 200 mm (measuring range: 1.8–350 μm) |
| Measuring time: | about 10 s (in the case of 200 mg) |
| Cycle time: | 10 ms |
| Start/stop at: | 1% on channel 28 |
| Dispersing gas: | compressed air |
| Pressure: | 3 bar |
| Vacuum: | maximum |
| Evaluation method: | HRLD |

Sample Preparation/Product Feed:

About 200 mg of the test substance are weighed onto a piece of card.

Using another piece of card all the larger lumps are broken up. The powder is transferred into the vibrating channel. A gap of 1.2 to 1.4 mm is set between the vibrating channel and funnel. After the start of the measurement the frequency of the vibrating channel is increased as continuously as possible to 100% towards the end of the measurement.

III) Determining the Specific Surface Area of Tiotropium Bromide Monohydrate, Micronised (1-Point BET Method):

Method:

The specific surface is determined by exposing the powder sample to a nitrogen/helium atmosphere at different pressures. Cooling the sample causes the nitrogen molecules to be condensed on the surface of the particles. The quantity of condensed nitrogen is determined by means of the change in the thermal heat conductivity of the nitrogen/helium mixture and the surface of the sample is calculated by means of the surface nitrogen requirement. Using this value and the weight of the sample, the specific surface is calculated.

| Equipment and materials: | |
|---|---|
| Measuring equipment: | Monosorb, Messrs Quantachrome |
| Heater: | Monotektor, Messrs Quantachrome |
| Measuring and drying gas: | nitrogen (5.0)/helium (4.6) 70/30, Messer Griesheim |

| -continued | |
|---|---|
| Equipment and materials: | |
| Adsorbate: | 30% nitrogen in helium |
| Coolant: | liquid nitrogen |
| Measuring cell: | with capillary tube, Messrs. W. Pabisch GmbH&Co.KG |
| Calibration peak; | 1000 µl, Messrs. Precision Sampling Corp. |
| Analytical scale: | R 160 P, Messrs. Satorius |

Calculating the Specific Surface:

The measured values are indicated by the equipment in [m$^2$] and are usually converted into [cm$^2$/g] on weighing (dry mass):

$$A_{spez} = \frac{MW * 10000}{m_{tr}}$$

$A_{spez}$=specific surface [cm$^2$/g]
MW=Measured value [m$^2$]
10000=conversion factor [cm$^2$/cm$^2$]

IV) Determining the Heat of Solution of Lactose (Enthalpy of Solution) $E_c$:

The solution enthalpy is determined using a solution calorimeter 2225 Precision Solution Calorimeter made by Messrs. Thermometric.

The heat of solution is calculated by means of the change in temperature occurring (as a result of the dissolving process) and the system-related change in temperature calculated from the base line.

Before and after the ampoule is broken, electrical calibration is carried out with an integrated heating resistor of a precisely known power. A known heat output is delivered to the system over a set period and the jump in temperature is determined.

Method and Equipment Parameters:

| | |
|---|---|
| Solution calorimeter: | 2225 Precision Solution Calorimeter, Messrs Thermometric |
| Reaction cell: | 100 ml |
| Thermistor resistance: | 30.0 kΩ (at 25° C.) |
| Speed of stirrer: | 500 U/min |
| Thermostat: | Thermostat of 2277 Thermal Activity Monitor TAM, Messrs Thermometric |
| Temperature: | 25° C. ± 0.0001° C. (over 24 h) |
| Measuring ampoules: | Crushing ampoules 1 ml, Messrs Thermometric |
| Seal: | Silicon stopper and beeswax, Messrs. Thermometric |
| Weight: | 40 to 50 mg |
| Solvent: | Chemically pure water |
| Volume of solvent: | 100 ml |
| Bath temperature: | 25° C. |
| Temperature resolution: | High |
| Starting temperature: | −40 mK (±10 mK) temperature-offset |
| Interface: | 2280-002 TAM accessory interface 50 Hz, Messrs Thermometric |
| Software: | SolCal V1.1 for WINDOWS |
| Evaluation: | Automatic evaluation with Menu point CALCULATION/ANALYSE EXPERIMENT. (Dynamics of base line; calibration after breakage of ampoule). |

Electrical Calibration:

The electrical calibration takes place during the measurement, once before and once after the breakage of the ampoule. The calibration after the breakage of the ampoule is used for the evaluation.

| | |
|---|---|
| Amount of heat: | 2.5 J |
| Heating power: | 500 mW |
| Heating time: | 10 s |
| Duration of base lines: | 5 min (before and after heating) |

V) Examples of Formulations

A) Inhalable Powders:

| Ingredients | µg per capsule |
|---|---|
| 1) | |
| tiotropium bromide monohydrate | 10.8 |
| 2a'-hydrochloride | 35 |
| lactose | 4954.2 |
| Total | 5000 |
| 2) | |
| tiotropium bromide monohydrate | 21.7 |
| 2a'-maleate salt | 75 |
| lactose | 4903.3 |
| Total | 5000 |
| 3) | |
| tiotropium bromide monohydrate | 22.5 |
| 2a'-maleate salt | 80.5 |
| lactose | 4897 |
| Total | 5000 |
| 4) | |
| tiotropium bromide × H2O | 22.5 |
| 2a'-maleate salt | 95.5 |
| lactose | 4828 |
| Total | 5000 |

B) Propellant-Driven Inhalable Aerosols:

| Ingredients | % by weight |
|---|---|
| 1) | |
| tiotropium bromide monohydrate | 0.015 |
| 2a'-hydrochloride | 0.066 |
| soya lecithin | 0.2 |
| TG134a:TG227 = 2:3 | ad 100 |
| 2) | |
| tiotropium bromide | 0.029 |
| compound 2a'-maleate salt | 0.033 |
| absolute ethanol | 0.5 |
| isopropyl myristate | 0.1 |
| TG 227 | ad 100 |

What is claimed is:

1. A composition comprising one or more salts of tiotropium 1 and one or more pharmacologically acceptable salts of a compound of formula

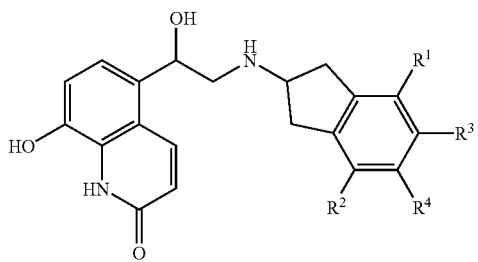

wherein
R$^1$ and R$^2$ are each hydrogen; and
R$^3$ and R$^4$ are each ethyl; together with a pharmaceutically acceptable carrier.

2. The composition according to claim 1 wherein the one or more salts of tiotropium 1 is in the form of the chloride, bromide, iodide, methanesulphonate, paratoluene sulphonate or methyl sulphate.

3. The composition according to claim 1 wherein the one or more salts of tiotropium 1 and the one or more pharmacologically acceptable salts of compound 2' are either present together in a single preparation or are contained in two separate preparations.

4. The composition according to claim 3 wherein the weight ratios of 1 to 2' are in the range from 1:300 to 30:1.

5. The composition according to claim 3 wherein a single application corresponds to a dosage of the combination of active substances 1 and 2' of 0.01 to 10000 μg.

6. The composition according to claim 4 that it is in the form of a formulation suitable for inhalation.

7. The composition according to claim 6 wherein the form is selected from the group consisting of inhalable powders, propellant-containing metering aerosols and propellant-free inhalable solutions or suspensions.

8. The composition according to claim 7 comprising an inhalable powder which contains 1 and 2' in admixture with suitable physiologically acceptable excipients selected from the group consisting of monosaccharides, disaccharides, oligo- and polysaccharides, polyalcohols, salts, and mixtures of these excipients.

9. The composition according to claim 8 wherein the excipient has a maximum average particle size of 250 μm.

10. The composition according to claim 8 contained in a capsule.

11. The composition according to claim 7 in the form of an inhalable powder consisting essentially of active substances 1 and 2'.

12. The composition according to claim 7 in the form of a propellant-containing inhalable aerosol comprising active substances 1 and 2' in dissolved or dispersed form.

13. The composition according to claim 7 in the form of a propellant-free inhalable solution or suspension comprising water, ethanol or a mixture of water and ethanol as a solvent.

14. A method for treating inflammatory or obstructive diseases of the respiratory tract comprising the administration to a patient of a therapeutically effective amount of the composition according to claim 1.

* * * * *